United States Patent
Tran et al.

(10) Patent No.: US 7,634,318 B2
(45) Date of Patent: Dec. 15, 2009

(54) MULTI-ELEMENT ACOUSTIC RECHARGING SYSTEM

(75) Inventors: Binh C. Tran, Minneapolis, MN (US); Robert S. Harguth, Ham Lake, MN (US); Bin Mi, Plymouth, MN (US); Keith R. Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 12/128,396

(22) Filed: May 28, 2008

(65) Prior Publication Data

US 2008/0312720 A1 Dec. 18, 2008

Related U.S. Application Data

(60) Provisional application No. 60/943,939, filed on Jun. 14, 2007.

(51) Int. Cl.
*A61N 1/08* (2006.01)
(52) U.S. Cl. ....................................................... 607/61
(58) Field of Classification Search ................... 607/61
See application file for complete search history.

(56) References Cited

U.S. PATENT DOCUMENTS

| | | |
|---|---|---|
| 2,967,957 A | 1/1961 | Massa |
| 3,568,661 A | 3/1971 | Franklin |
| 3,676,720 A | 7/1972 | Libby et al. |
| 3,757,770 A | 9/1973 | Brayshaw et al. |
| 3,792,204 A | 2/1974 | Murayama et al. |
| 3,798,473 A | 3/1974 | Murayama et al. |
| 3,832,580 A | 8/1974 | Yamamuro et al. |
| 3,894,198 A | 7/1975 | Murayama et al. |
| 3,940,637 A | 2/1976 | Ohigashi et al. |
| 3,978,353 A | 8/1976 | Kinoshita |
| 4,008,408 A | 2/1977 | Kodama |
| 4,051,455 A | 9/1977 | Fowler |
| 4,056,742 A | 11/1977 | Tibbetts |
| 4,064,375 A | 12/1977 | Russell et al. |
| 4,096,756 A | 6/1978 | Alphonse |
| 4,127,110 A | 11/1978 | Bullara |
| 4,170,742 A | 10/1979 | Itagaki et al. |
| 4,181,864 A | 1/1980 | Etzold |

(Continued)

FOREIGN PATENT DOCUMENTS

DE 3222349 1/1984

(Continued)

OTHER PUBLICATIONS

U.S. Appl. No. 61/027,983, filed Feb. 12, 2008.

(Continued)

*Primary Examiner*—Mark W Bockelman
*Assistant Examiner*—Eric D Bertram
(74) *Attorney, Agent, or Firm*—Faegre & Benson LLP

(57) ABSTRACT

An acoustic energy delivery system for delivering acoustic energy to an implantable medical device ("IMD"). The system includes an IMD having a power source and an energy delivery device. The energy delivery device includes a controller and an array of ultrasonic elements electrically coupled to the controller and configured to deliver acoustic energy to the IMD. Methods of delivering acoustic energy to an IMD are also disclosed.

17 Claims, 6 Drawing Sheets

U.S. PATENT DOCUMENTS

| | | |
|---|---|---|
| 4,227,407 A | 10/1980 | Drost |
| 4,281,484 A | 8/1981 | Massa |
| 4,431,873 A | 2/1984 | Dunn et al. |
| 4,433,400 A | 2/1984 | De Reggi et al. |
| 4,456,850 A | 6/1984 | Inoue et al. |
| 4,481,950 A | 11/1984 | Duggan |
| 4,517,665 A | 5/1985 | De Reggi et al. |
| 4,519,401 A | 5/1985 | Ko et al. |
| 4,541,431 A | 9/1985 | Ibrahim et al. |
| 4,558,249 A | 12/1985 | Lerch et al. |
| 4,580,074 A | 4/1986 | Gilman |
| 4,593,703 A | 6/1986 | Cosman |
| 4,600,855 A | 7/1986 | Strachan |
| 4,642,508 A | 2/1987 | Suzuki et al. |
| 4,653,036 A | 3/1987 | Harris et al. |
| 4,653,508 A | 3/1987 | Cosman |
| 4,660,568 A | 4/1987 | Cosman |
| 4,672,976 A | 6/1987 | Kroll |
| 4,676,255 A | 6/1987 | Cosman |
| 4,677,337 A | 6/1987 | Kleinschmidt et al. |
| 4,781,715 A | 11/1988 | Wurzel |
| 4,793,825 A | 12/1988 | Benjamin et al. |
| 4,835,435 A | 5/1989 | Yeung et al. |
| 4,846,191 A | 7/1989 | Brockway et al. |
| 4,911,172 A | 3/1990 | Bui et al. |
| 4,958,100 A | 9/1990 | Crawley et al. |
| 5,012,815 A | 5/1991 | Bennett, Jr. et al. |
| 5,024,224 A | 6/1991 | Engebretson |
| 5,088,576 A | 2/1992 | Potthoff et al. |
| 5,113,859 A | 5/1992 | Funke |
| 5,160,870 A | 11/1992 | Carson et al. |
| 5,178,153 A | 1/1993 | Einzig |
| 5,283,397 A | 2/1994 | Pavlovic |
| 5,289,821 A | 3/1994 | Swartz |
| 5,300,875 A | 4/1994 | Tuttle |
| 5,314,457 A | 5/1994 | Jeutter et al. |
| 5,339,290 A | 8/1994 | Greenstein |
| 5,367,500 A | 11/1994 | Ng |
| 5,381,067 A | 1/1995 | Greenstein et al. |
| 5,381,386 A | 1/1995 | Lum et al. |
| 5,410,587 A | 4/1995 | Grunwell |
| 5,411,551 A | 5/1995 | Winston et al. |
| 5,423,334 A | 6/1995 | Jordan |
| 5,438,553 A | 8/1995 | Wilson et al. |
| 5,476,488 A | 12/1995 | Morgan et al. |
| 5,483,501 A | 1/1996 | Park et al. |
| 5,488,954 A | 2/1996 | Sleva et al. |
| 5,495,137 A | 2/1996 | Park et al. |
| 5,554,177 A | 9/1996 | Kieval et al. |
| 5,562,714 A | 10/1996 | Grevious |
| 5,571,152 A | 11/1996 | Chen et al. |
| 5,628,782 A | 5/1997 | Myers et al. |
| 5,679,026 A | 10/1997 | Fain et al. |
| 5,704,352 A | 1/1998 | Tremblay et al. |
| 5,733,313 A | 3/1998 | Barreras, Sr. et al. |
| 5,735,887 A | 4/1998 | Barreras, Sr. et al. |
| 5,741,316 A | 4/1998 | Chen et al. |
| 5,749,909 A | 5/1998 | Schroeppel et al. |
| 5,757,104 A | 5/1998 | Getman et al. |
| 5,792,195 A | 8/1998 | Carlson et al. |
| 5,807,258 A | 9/1998 | Cimochowski et al. |
| 5,825,117 A | 10/1998 | Ossmann et al. |
| 5,832,924 A | 11/1998 | Archibald et al. |
| 5,833,603 A | 11/1998 | Kovacs et al. |
| 5,843,135 A | 12/1998 | Weijand et al. |
| 5,873,835 A | 2/1999 | Hastings et al. |
| 5,879,283 A | 3/1999 | Adams et al. |
| 5,935,081 A | 8/1999 | Kadhiresan |
| 5,956,292 A | 9/1999 | Bernstein |
| 5,957,950 A | 9/1999 | Mockros et al. |
| 5,967,986 A | 10/1999 | Cimochowski et al. |
| 6,044,298 A | 3/2000 | Salo et al. |
| 6,053,873 A | 4/2000 | Govari et al. |
| 6,058,329 A | 5/2000 | Salo et al. |
| 6,068,589 A | 5/2000 | Neukermans |
| 6,082,367 A | 7/2000 | Greeninger et al. |
| 6,140,740 A | 10/2000 | Porat et al. |
| 6,185,452 B1 | 2/2001 | Schulman et al. |
| 6,223,081 B1 | 4/2001 | Kerver |
| 6,409,675 B1 | 6/2002 | Turcott |
| 6,475,170 B1 | 11/2002 | Doron et al. |
| 6,477,406 B1 | 11/2002 | Turcott |
| 6,480,733 B1 | 11/2002 | Turcott |
| 6,486,588 B2 | 11/2002 | Doron et al. |
| 6,504,289 B2 | 1/2003 | Toda et al. |
| 6,527,729 B1 | 3/2003 | Turcott |
| 6,537,200 B2 | 3/2003 | Leysieffer et al. |
| 6,554,761 B1 | 4/2003 | Puria et al. |
| 6,575,894 B2 | 6/2003 | Leysieffer et al. |
| 6,600,949 B1 | 7/2003 | Turcott |
| 6,628,989 B1 | 9/2003 | Penner et al. |
| 6,629,922 B1 | 10/2003 | Puria et al. |
| 6,643,548 B1 | 11/2003 | Mai et al. |
| 6,645,145 B1 | 11/2003 | Dreschel et al. |
| 6,654,638 B1 | 11/2003 | Sweeney |
| 6,671,550 B2 | 12/2003 | Iaizzo et al. |
| 6,697,674 B2 | 2/2004 | Leysieffer |
| 6,740,076 B2 | 5/2004 | Hoben et al. |
| 6,741,714 B2 | 5/2004 | Jensen |
| 6,763,722 B2 | 7/2004 | Fjield et al. |
| 6,764,446 B2 | 7/2004 | Wolinsky et al. |
| 6,772,490 B2 | 8/2004 | Toda |
| 6,792,308 B2 | 9/2004 | Corbucci |
| 7,016,739 B2 | 3/2006 | Bange et al. |
| 7,024,248 B2 | 4/2006 | Penner et al. |
| 7,035,684 B2 | 4/2006 | Lee |
| 7,107,103 B2 | 9/2006 | Schulman et al. |
| 7,114,502 B2 | 10/2006 | Schulman et al. |
| 7,115,096 B2 | 10/2006 | Siejko et al. |
| 7,118,531 B2 | 10/2006 | Krill |
| 7,123,962 B2 | 10/2006 | Siejko et al. |
| 7,127,290 B2 | 10/2006 | Girouard et al. |
| 7,176,602 B2 | 2/2007 | Schlenke |
| 7,198,603 B2 | 4/2007 | Penner et al. |
| 7,220,232 B2 | 5/2007 | Suorsa et al. |
| 7,228,175 B2 | 6/2007 | Jain et al. |
| 7,236,821 B2 | 6/2007 | Cates et al. |
| 7,248,923 B2 | 7/2007 | Maile et al. |
| 7,260,429 B2 | 8/2007 | Siejko et al. |
| 7,273,457 B2 | 9/2007 | Penner |
| 7,283,874 B2 | 10/2007 | Penner |
| 7,335,169 B2 | 2/2008 | Thompson et al. |
| 7,431,699 B2 | 10/2008 | Whitehurst et al. |
| 2002/0045921 A1 | 4/2002 | Wolinsky et al. |
| 2002/0077673 A1 | 6/2002 | Penner et al. |
| 2004/0106954 A1 | 6/2004 | Whitehurst et al. |
| 2004/0122484 A1 | 6/2004 | Hatlestad et al. |
| 2004/0127792 A1 | 7/2004 | Siejko et al. |
| 2004/0138572 A1 | 7/2004 | Thiagarajan |
| 2004/0230249 A1 | 11/2004 | Haefner |
| 2004/0260214 A1 | 12/2004 | Echt et al. |
| 2005/0131472 A1 | 6/2005 | Ding et al. |
| 2005/0137490 A1 | 6/2005 | Scheiner et al. |
| 2005/0149138 A1 | 7/2005 | Min et al. |
| 2006/0009818 A1 | 1/2006 | Von Arx et al. |
| 2006/0136004 A1* | 6/2006 | Cowan et al. ............... 607/33 |
| 2006/0142819 A1 | 6/2006 | Penner et al. |
| 2006/0149329 A1 | 7/2006 | Penner |
| 2007/0049977 A1 | 3/2007 | Von Arx et al. |
| 2007/0055184 A1* | 3/2007 | Echt et al. ................ 601/2 |
| 2007/0093875 A1 | 4/2007 | Chavan et al. |
| 2008/0021289 A1 | 1/2008 | Zhang et al. |
| 2008/0021509 A1 | 1/2008 | Mi et al. |

| | | |
|---|---|---|
| 2008/0021510 | A1 | 1/2008 Mi et al. |

FOREIGN PATENT DOCUMENTS

| | | |
|---|---|---|
| EP | 0798016 | 10/1997 |
| EP | 0897690 | 2/1999 |
| EP | 1151719 | 11/2001 |
| WO | WO 83/03345 | 10/1983 |
| WO | WO 97/01986 | 1/1997 |
| WO | WO 97/33513 | 9/1997 |
| WO | WO 97/35636 | 10/1997 |
| WO | WO 97/47236 | 12/1997 |
| WO | WO 98/26716 | 6/1998 |
| WO | WO 98/29030 | 7/1998 |
| WO | WO 99/26530 | 6/1999 |
| WO | WO 99/59460 | 11/1999 |
| WO | WO 00/16686 | 3/2000 |
| WO | WO 03/068047 | 8/2003 |
| WO | WO 2004/091719 | 10/2004 |
| WO | WO 2006/069215 | 6/2006 |

OTHER PUBLICATIONS

Fink, "Time Reversal of Ultrasonic Fields—Part 1: Basic Principles," IEEE Transactions on Ultrasonics, Ferroelectrics, and Frequency Control, vol. 39, No. 5, Sep. 1992, pp. 555-566.

Wu et al., "Time Reversal of Ultrasonic Fields—Part 2: Experimental Results," IEEE Transactions on Ultrasonics, Ferroelectrics, and Frequency Control, vol. 39, No. 5, Sep. 1992, pp. 567-578.

Cassereau et al., "Time Reversal of Ultrasonic Fields—Part 3: Theory of the Closed Time-Reversal Cavity," IEEE Transactions on Ultrasonics, Ferroelectrics, and Frequency Control, vol. 39, No. 5, Sep. 1992, pp. 579-592.

Fink et al., "Time Reversal Acoustics," 2004 IEEE Transactions on Ultrasonics, Ferroelectrics, and Frequency Control Joint 50th Anniversary Conference, Ultrasonics Symposium, pp. 850-859.

Blevins Ph.D., "Formulas for Natural Frequency and Mode Shape", ISBN: 1-57524-184-6.

C. Hierold et al (Germany, 1998) "Implantable Low Power Integrated Pressure Sensor System for Minimal Invasive Telemetric Patient Monitoring" IEEE, pp. 568-573.

ER. Cosman et al (Massachussetts, Apr. 1979) "A Telemetric Pressure Sensor for Ventricular Shunt Systems" Surgical Neurology, vol. 11, No. 4, pp. 287-294.

G. W. H. Schurink et al (1998) "Late Endoleak after Endovascular Therapy for Abdominal Aortic Aneurysm" Eur. J. Vasc. Endovasc. Surg. vol. 17, pp. 448-450.

GH White et al (1997) "Endoleak Following Endoluminal Repair of AAA: Management Options and Patient Outcomes", J. Endovasc Surg. p. I-45.

Karl E. Richard et al (Germany, Jan. 1999) "First clinical results with a telemetric shunt-integrated ICP-sensor" Neurological Research vol. 21, pp. 117-120.

Prof. Dr. Johannes Zacheja et al (Germany, Sep. 1996) "An Implantable Microsystem for Biomedical Applications" Micro System Technologies 96, pp. 717-722.

S. K. Gupta et al (1999) "Use of a Piezoelectric Film Sensor for Monitoring Vascular Grafts" The American Journal of Surgery vol. 160, pp. 182-186.

T. Chuter et al (Sweden, Jan. 1997) "Aneurysm Pressure following Endovascular Exclusion" Eur. J. Vasc. Endovasc. Surg. vol. 13, pp. 85-87.

T.A. Cochran et al (1990) "Aortic Aneurysm Abdominal", Current Therapy in Adult Medicine, Fourth Edition.

Z. Tang et al (May 1995) "Data Transmission from an Implantable Biotelemeter by Load-Shift Keying Using Circuit Configuration Modulator" IEEE Transactions on Biomedical Engineering, vol. 42, No. 5, pp. 524-528.

International Search Report and Written Opinion from related case PCT/US2008/064994, mailed Dec. 22, 2008, 17 pp.

* cited by examiner

MULTI-ELEMENT ACOUSTIC RECHARGING SYSTEM

CROSS REFERENCE TO RELATED APPLICATION

The present application claims priority under 35 U.S.C. § 119 to U.S. Provisional Patent Application No. 60/943,939, filed Jun. 14, 2007, entitled "Multi-Element Acoustic Recharging System," which is incorporated herein by reference in its entirety.

TECHNICAL FIELD

The present invention relates to implantable medical devices and methods of delivering energy to implantable medical devices. More specifically, the invention relates to devices and methods used to deliver energy to an implantable medical device using a device located external to a patient's body.

BACKGROUND

Implantable medical devices are used to treat a variety of medical conditions. Examples of implantable medical devices include drug delivery devices, pain management devices, and devices that treat heart rhythm disorders. Examples of implantable medical devices that treat heart rhythm disorders are cardiac pacemakers, implantable cardioverter defibrillators, and cardiac resynchronization therapy ("CRT") devices. A cardiac pacemaker is commonly used to treat bradycardia. An implantable cardioverter defibrillator ("ICD") is commonly used to treat tachycardia. A CRT device is commonly used to treat heart failure associated dyssynchrony. These devices generally include a pulse generator and one or more leads that deliver electrical energy to the heart. The pulse generator typically includes a housing for a battery and electrical circuitry and a header for connecting the leads to the pulse generator. Other examples of implantable medical devices include remote devices with sensing, monitoring and/or stimulating functions. For example, implantable pressure sensors can be located in the vasculature and used in conjunction with pacemakers, CRT devices, and ICDs.

At some point, the battery or power source within an implantable medical device runs out of energy. Generally, this energy depletion requires replacement of the implantable medical device. These devices, and others, may include a rechargeable power source to extend their usable lifetime. Due to the nature of implantable medical devices, methods for recharging are typically indirect, utilizing an external device not physically connected to the implantable medical device. One method of recharging the power source of an implantable medical device is by the conversion of acoustic energy to electrical energy. Using ultrasonic transducers, for example, acoustic energy can be transmitted through the body to the implantable medical device for recharging the electrical power source. Current technologies for acoustically charging a power source of an implantable medical device, however, are sometimes inefficient. Thus, there is a need for an improved device and method for delivering acoustic energy to implantable medical devices.

SUMMARY

In one embodiment, the invention is an acoustic energy delivery system for delivering acoustic energy to an implantable medical device ("IMD"). The system comprises an acoustic energy delivery device and an IMD. The acoustic energy delivery device includes a power source, a controller, and a multi-element array of ultrasonic elements configured to deliver acoustic energy through the body to the IMD. In some embodiments, the IMD includes an energizable power source and an acoustic transducer to receive acoustic energy delivered by the energy delivery device. In use, the controller is configured to selectively control one or more of the ultrasonic elements within the array to manipulate the delivery of acoustic energy through the body.

In another embodiment, the invention includes a method of controlling an energy delivery device for delivering acoustic energy to an IMD. In one embodiment, the method comprises sending one or more signals to an IMD and processing one or more responsive signals sent by the IMD. The energy delivery device is configured to operate based upon the responsive signals received from the IMD. An array of ultrasonic elements is electrically coupled to a controller, allowing the controller to control the excitation of each transducer element or subsets of transducer elements to more effectively deliver acoustic energy to the IMD. In some embodiments, the one or more signals sent to the IMD causes the IMD to enter into a charging mode and send out a plurality of test pulses to an energy delivery device having an array of ultrasonic elements.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
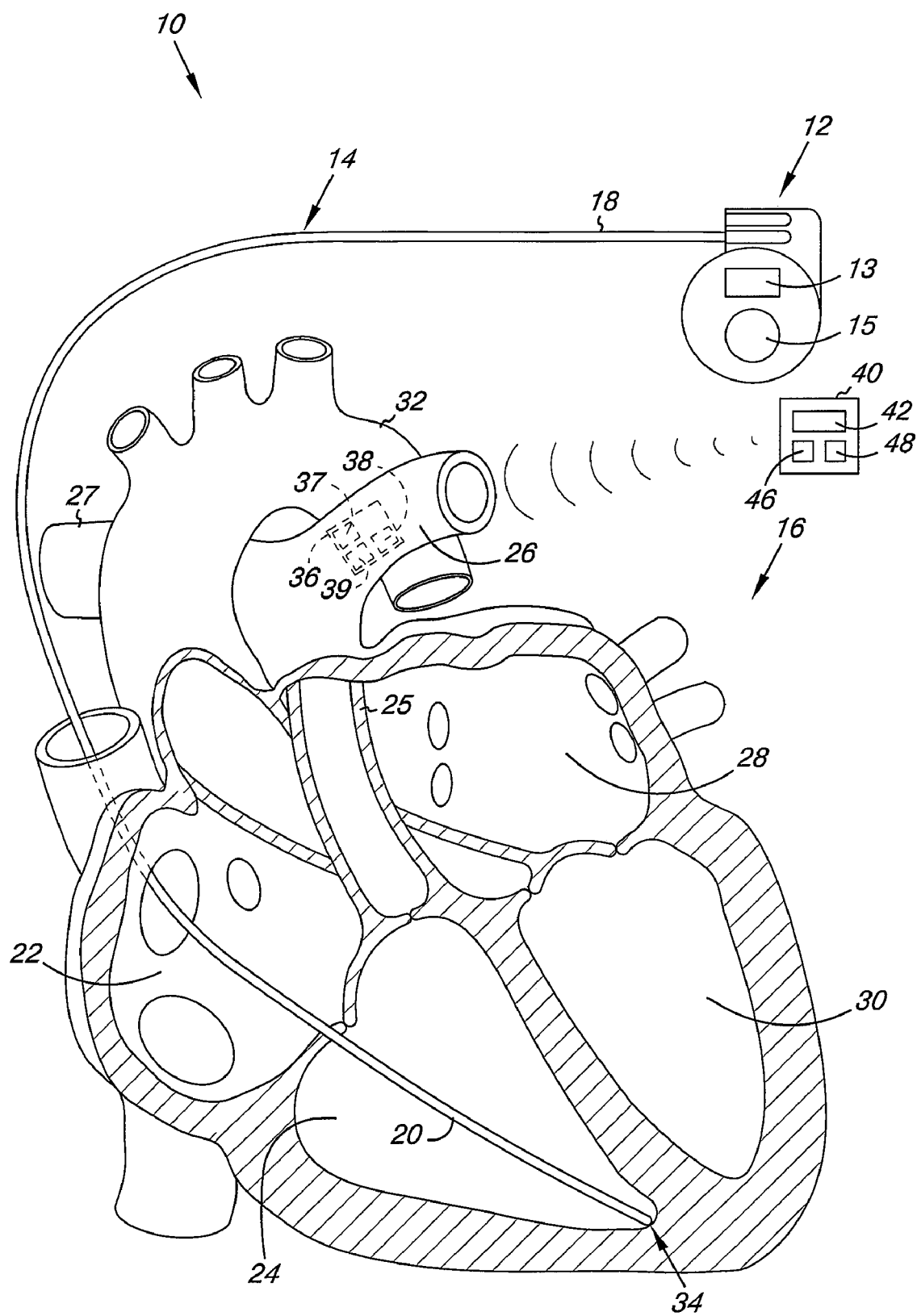
FIG. 1 is a combined cutaway and perspective view of a multi-element acoustic energy delivery system according to one embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a combined cutaway and perspective view of an acoustic energy delivery system 10 according to one embodiment of the present invention. In the embodiment shown in FIG. 1, the system 10 includes a pulse generator 12 having a power source 13, a cardiac lead 14, and an acoustic transducer 15. The lead 14 operates to convey electrical signals between the heart 16 and the pulse generator 12. A proximal end 18 of the lead 14 is coupled to the pulse generator 12 and a distal end 20 is coupled to the heart 16. The heart 16 includes a right atrium 22, a right ventricle 24, and a main pulmonary artery 25. The heart 16 also includes a left atrium 28, a left ventricle 30, and an aorta 32. In the embodiment shown, the system 10 includes one lead 14, but in other embodiments, the system 10 includes a plurality of leads 14. For example, the system 10 may include a first lead 14 adapted to convey electrical signals between the pulse generator 12 and the left ventricle 30 and a second lead 14 adapted to convey electrical signals between the pulse generator 12 and the right ventricle 24.

In the embodiment of FIG. 1, an electrode 34 is positioned in the right ventricle 24. When positioned as shown, the electrode 34 can be used to sense the electrical activity of the heart 16 and/or to apply a stimulating pulse to the right ventricle 24. In other embodiments, the cardiac lead 14 can also be implanted in other portions of the heart 16 as known in the art. For example, the lead 14 may be implanted in the right atrium 22, the left atrium 28, the left ventricle 30, or in the coronary veins (e.g., for bi-ventricular pacing and/or heart failure treatment). In one embodiment, the cardiac lead 14 includes multiple electrodes 34. In some embodiments, the lead 14 is an epicardial lead.

The system 10 includes a remote implantable medical device 36, which has a power source 37, an acoustic transducer 38, and circuitry 39 in addition to other components related to the IMD 36 function. In some embodiments, the system 10 also includes an energy delivery device 40, which has a multi-element transducer array 42, a power source 46, and a controller 48. In the embodiment shown in FIG. 1, the energy delivery device 40 is used to deliver acoustic energy to the IMD 36 (shown in FIG. 1 as waves emanating from the energy delivery device 40 toward the IMD 36). The transducer 38 in the IMD 36 converts acoustic energy to electrical energy, which can then be used immediately, in the short term, or stored for later use by the IMD 36 depending on the power source 48. The power source 37 in the IMD 36 can be a rechargeable battery, a capacitor, or any other energy source for providing electrical operating power to various components of the IMD 36. The energy delivery device 40 is electronically reconfigurable by utilizing the controller 48 to adjust excitation parameters such as timing, phase, amplitude, and/or frequency of the multi-element transducer 42, and is thus able to deliver a range of acoustic fields to the IMD 36 to increase efficiency in recharging. In other embodiments, the energy delivery device 40 can deliver acoustic energy to the acoustic transducer 15 of the pulse generator 12 or to any other implantable medical device in place of or in addition to the IMD 36.

The IMD 36 shown in FIG. 1 is a pressure sensor for measuring pulmonary arterial pressure. Although the IMD 36 is shown in the left pulmonary artery 26, in other embodiments, the IMD 36 may be implanted in the main pulmonary artery 25 or in the right pulmonary artery 27. In other embodiments, the IMD 36 can be configured to measure other physiological parameters such as, for example, temperature, blood or fluid flow, strain, and/or electrical, chemical or magnetic properties within the body.

In other embodiments, the IMD 36 may be implanted in other regions of the patient's vasculature, in other body lumens, or in other areas of the body, and may comprise any type of chronically implanted device or remote sensor adapted to deliver therapy or monitor biological and chemical parameters, properties, and functions. For example, the IMD 36 could comprise a glucose level monitor, a pulmonary sound sensor, a satellite pacing device, or any other remote sensing or therapy-delivering device. In other embodiments, the IMD 36 could sense, measure, calculate, or derive associated parameters such as, for example, the flow rate, the maximum and minimum pressure, and the time rate change (slope) of the pressure. In some embodiments, a plurality of remote implantable medical devices 36 are implanted throughout the body, and are configured to receive acoustic signals from the energy delivery device 40.

Figure 2:
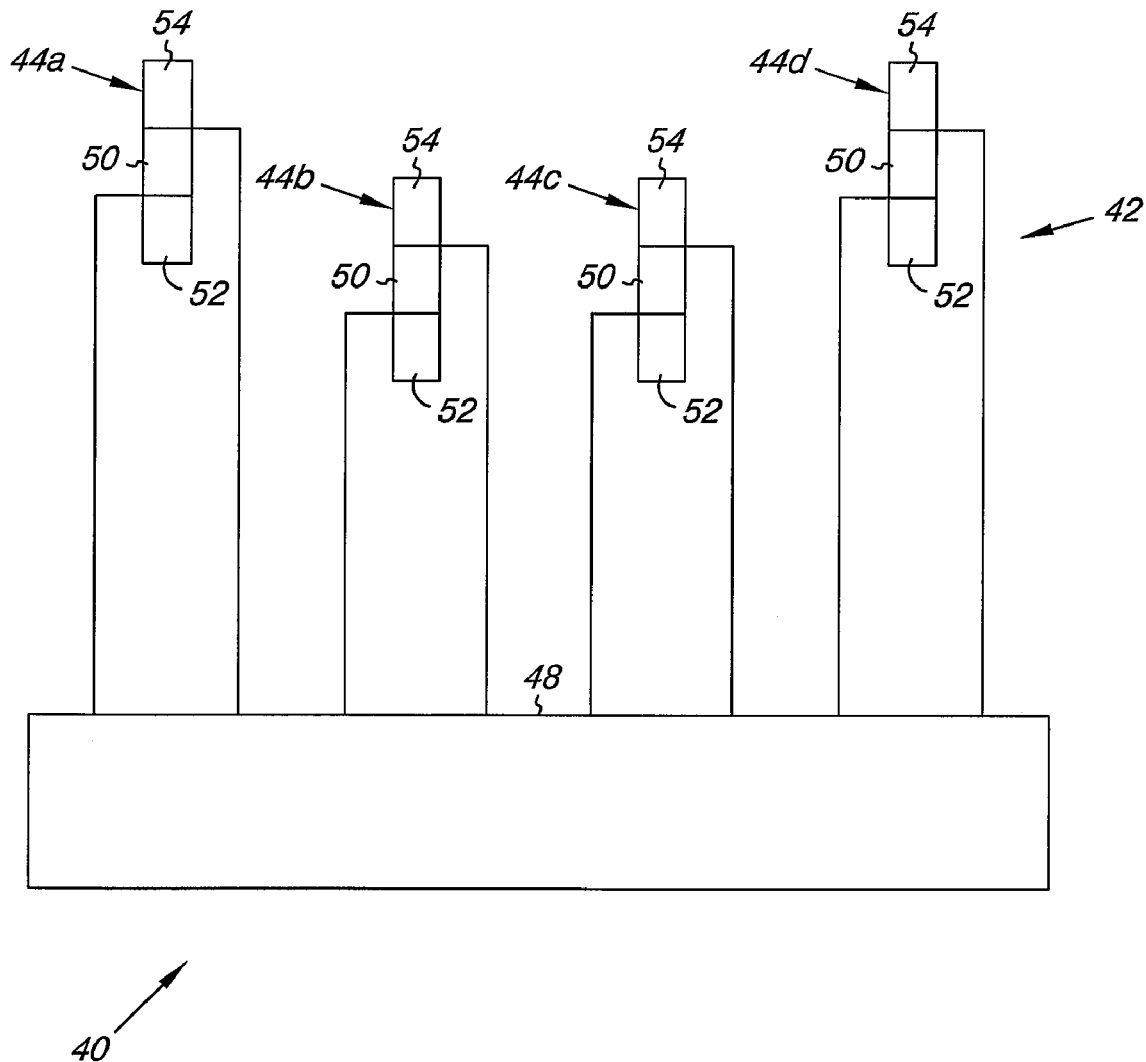
FIG. 2 is a schematic view of the multi-element energy delivery device of FIG. 1 according to one embodiment of the present invention.

FIG. 2 is a schematic view of one embodiment of the energy delivery device 40 of FIG. 1. In the illustrated embodiment, the energy delivery device 40 includes an array 42 of ultrasonic elements 44. The array 42 is used to transmit an acoustic energy signal to and efficiently recharge the power source 37 in the IMD 36. Use of the array 42 in some embodiments may enable an increase in energy transfer efficiency. The ultrasonic elements 44 are electrically coupled to the controller 48, which can be a microprocessor, an integrated circuit, or any other processor or circuitry that can be used for operating the array 42. In some embodiments, the controller 48 selectively controls each ultrasonic element 44 individually such that the multi-element array 42 functions as a combination of ultrasonic elements 44. In one embodiment, for example, the controller 48 operates all ultrasonic elements 44 simultaneously and in-phase as if the array 42 were a single ultrasonic element. In other embodiments, the controller 48 operates all or some of the ultrasonic elements 44 with phase delays and/or amplitude modulations, electronically changing the effective aperture of the array 42. In still other embodiments, the controller 48 operates a single ultrasonic element 44 or a subset of ultrasonic elements 44. The controller 48 determines the appropriate configuration for transmission of acoustic energy from the array 42 to the IMD 36 and controls the operation of the ultrasonic elements 44 accordingly, as discussed further herein, for example, with respect to FIGS. 3-4. In some embodiments, the controller 48 utilizes feedback to determine the appropriate transmission configuration. In other embodiments, the controller 48 operates the transducer elements 44 without feedback.

In the embodiment shown in FIG. 2, the array 42 includes four ultrasonic elements 44, but in other embodiments, the array 42 can include any number of ultrasonic elements 44. In one embodiment, the ultrasonic elements 44 operate at the same frequency. In other embodiments, the ultrasonic elements 44 do not all operate at the same frequency. In one embodiment, the ultrasonic elements 44 operate at a frequency of between about 20 kHz to about 200 kHz. In one embodiment, the ultrasonic elements 44 operate at a center frequency of about 40 kHz. In one embodiment, all of the ultrasonic elements 44 have the same resonant frequency, but in other embodiments, the ultrasonic elements 44 do not all have the same resonant frequency.

In the embodiment illustrated in FIG. 2, the ultrasonic elements 44 are piezoelectric elements including an active piezoelectric layer 50, a backing layer 52, and a front matching layer 54. The general principles of operation of piezoelectric elements are well known in the art. Briefly, the application of an AC voltage across electrodes coupled to the piezoelectric layer 50 causes the piezoelectric layer 50 to oscillate at the frequency of the applied voltage and produce an outward acoustic wave. In one embodiment, the piezoelectric layer 50 is made from a piezopolymer, piezoceramic, or piezocomposite material. In one embodiment, the piezoelectric layer 50 is a polyvinylidine difluoride ("PVDF") material. In another embodiment, the piezoelectric layer 50 is a lead zirconate titanate ("PZT") material. The ultrasonic elements 44 can have a variety of shapes and physical arrangements to maximize energy delivery to the IMD, as shown, for example, in FIGS. 5-9.

In the embodiment shown in FIG. 2, the backing layer 52 provides mechanical support and absorbs reflected acoustic energy. In one embodiment, the matching layer 54 provides an acoustic impedance match between the active layer 50 and the patient's skin, increasing energy transmission into the body. The matching layer 54 may be comprised of multiple layers to achieve the optimal acoustic impedance match. The piezoelectric layer 50, backing layer 52, and front matching layer 54 have a high coupling coefficient. The high coupling coefficient results in a high sensitivity of the ultrasonic element 44 and a high signal to noise ratio. The high coupling coefficient also allows for a larger bandwidth, thereby allowing for a high energy transfer level and a low reverberation level. The delivery of acoustic energy from an external energy delivery device 40 to an IMD 36 located within a patient often requires transmission through a complex, indirect, and lossy propagation path. Propagation is often indirect and multipath through attenuating body tissues and reflecting tissue interfaces resulting from different acoustic impedances in tissues such as skin, bones, lungs, muscles, and blood. Despite these complexities, the energy delivery device 40 can be used to reduce propagation losses and more efficiently deliver energy to the power source 38 within the implantable medical device 36.

Figure 3:
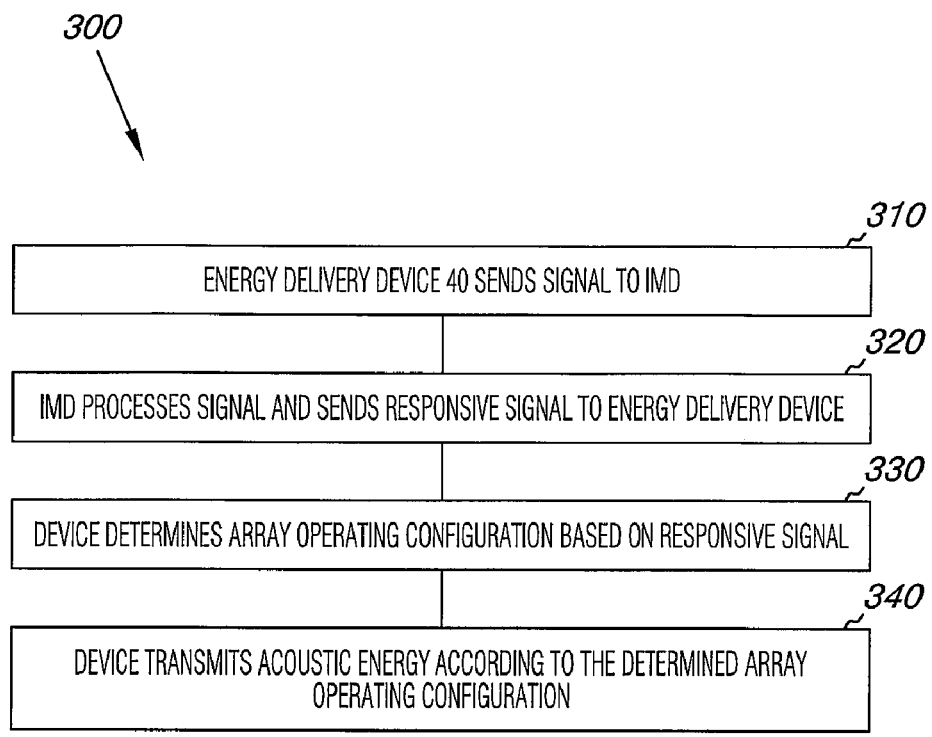
FIG. 3 is a flowchart illustrating a method of controlling the multi-element array of FIG. 2 according to one embodiment of the present invention.

FIG. 3 illustrates an illustrative method 300 of controlling the multi-element array 42 of FIG. 2 according to one embodiment of the present invention. As shown in FIG. 3, the energy delivery device 40 sends a signal to the implantable medical device 36 (block 310). The signal can be a ping, a series of pings, an instruction, or a command. The remote implantable medical device 36 receives and processes the signal and sends a responsive signal back to the device 40 (block 320). The responsive signal can be a generic transmission signal, an encoded measurement of the signal strength received from the energy delivery device 40, or some other signal. The energy delivery device 40 then determines the operating configuration of the array 42 producing the most efficient recharging based on the responsive signal (block 330) and configures the controller 48 to operate the ultrasonic elements 44 to transmit the acoustic energy according to that determined configuration (block 340).

In one implementation of method 300, for example, the controller 48 determines which ultrasonic elements 44 have a minimum attenuation in the acoustic path to the IMD 36 and operates only those ultrasonic elements 44 having the minimum attenuation in the acoustic path or those elements 44 having the least attenuating path. In one embodiment, the controller 48 determines which elements have minimum attenuation by first transmitting a signal from each element 44 individually to the IMD 36 and then receiving a response from the IMD 36. In one embodiment, the response from the IMD is a measurement of the acoustic signal amplitude of the IMD 36 received from the signal transmitted by each individual element 44 of the energy delivery device 40. In this embodiment, a response with a higher signal amplitude measurement may indicate less attenuation along the acoustic path than a response with a lower signal amplitude measurement. In another embodiment, the response from the IMD 36 is its standard response signal (e.g., an acknowledgement signal of known frequency and amplitude), and controller 48 determines the ultrasonic elements 44 having minimum attenuation by comparing the amplitude of the response signal received by the individual ultrasonic elements 44. The determination of whether the acoustic signal is sufficient can be determined, for example, by comparing the acoustic signal level received against a preset threshold programmed within the controller 48. In an alternative embodiment, the controller 48 operates a subset of the ultrasonic elements 44 that have a minimum attenuation in the acoustic path rather than a single ultrasonic element 44.

In another implementation of method 300, the controller 48 incorporates time reversal techniques to optimize the delivery of the acoustic energy to the IMD 36. Time reversal techniques enable phase alignment of acoustic fields at a desired target when the target's location is not precisely known or is changing. An illustrative technique for optimizing recharging efficiency using time reversal techniques is described, for example, in co-pending U.S. Provisional Patent Application Ser. No. 61/027,983, entitled, "Systems and Methods For Controlling Wireless Signal Transfers Between Ultrasound Enabled Medical Devices," which is incorporated herein by reference in its entirety. In some embodiments, the time reversal process is implemented according to method 300. The energy delivery device 40 transmits an acoustic signal towards the IMD 36. The IMD 36 receives the acoustic signal and, in response, transmits a series of signals back to the energy delivery device 40. The signals from the IMD 36 are received by the individual ultrasonic elements 44. The controller 48 may then analyze the received signals, determine the phase and amplitude differences between the received signals, and compute compensation factors. The controller 48 then applies these compensation factors to control the ultrasonic elements 44 in order to deliver the acoustic energy to the IMD 36.

Figure 4:
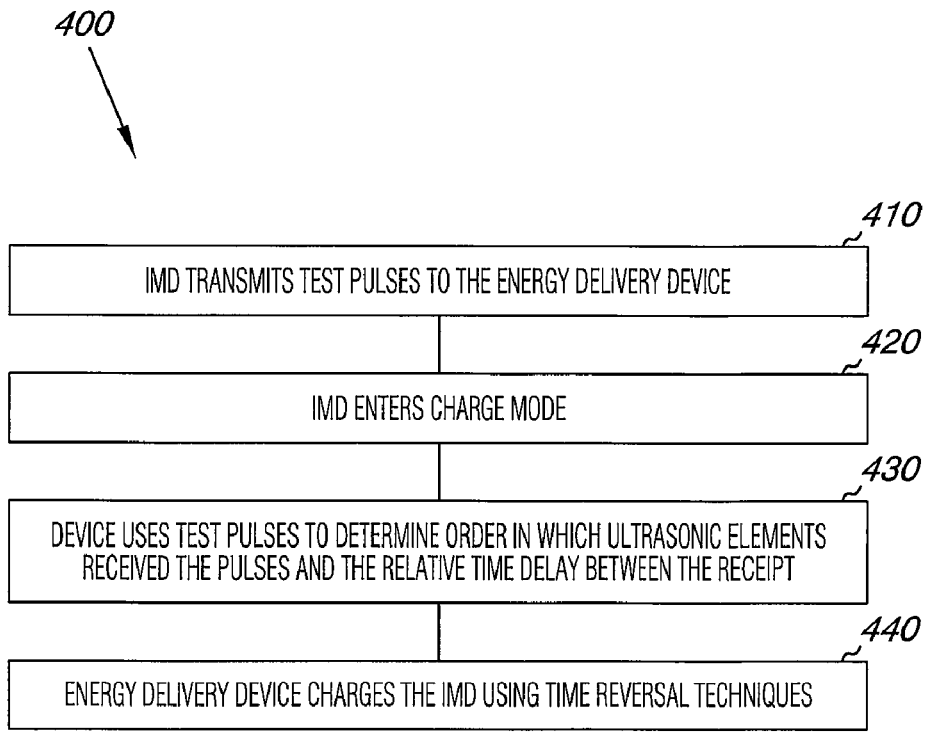
FIG. 4 is a flowchart illustrating a method of using a multi-element energy delivery device to send a test pulse to an implantable medical device according to one embodiment of the present invention.

FIG. 4 is a flowchart showing an exemplary method 400 of processing a test pulse sent from the IMD 36 to the energy delivery device 40 using time reversal techniques according to one embodiment of the present invention. As shown in FIG. 4, the IMD 36 transmits test pulses to the energy delivery device 40 (block 410). The test pulses can be any type of pulse. In one embodiment, for example, the test pulses are eight "1" bit pulses. The IMD 36 then enters into a charging mode (block 420). The energy delivery device 40 receives the test pulses on each ultrasonic element 44 of the device 40 and uses these pulses to determine the relative time delays between the signals received at each element 44 (block 430). The energy delivery device 40 transmits acoustic energy from the ultrasonic elements 44 using time reversal techniques. In one embodiment, for example, the energy delivery device 40 transmits acoustic energy in the opposite order from the order in which the device 40 received the test pulses and incorporating the relative time delays (block 440). Using the energy delivery device 40 shown in FIG. 2 as an example, if the charges received on elements 44a, 44b, 44c, and 44d are received in the order 44a, 44c, 44d, and 44b having a relative delay between 44a and 44c of one second, the charging would occur in the order 44b, 44d, 44c, 44a with a one second transmit delay between 44c and 44a.

The methods described herein can be used at any time during the charging cycle. In one embodiment, the controller 48 electronically reconfigures the control of the array 42 to compensate for changes in location of the IMD 36 from a previous position due to a change in body position, organ movement, respiration, and/or for other reasons. In some embodiments, the controller 48 incorporates information regarding physiological patterns (e.g., respiratory rate, cardiac cycle, etc.) and controls the array 42 based upon the pattern information. In one embodiment, the method is used at the beginning of the charging cycle. In another embodiment, the method is used during the charging cycle. In one embodiment, the method is used during the charging cycle and is initiated when a charge pause occurs in the charging cycle. In some embodiments, the charge pause is a programmable event in the controller 48 and is used to re-evaluate the efficiency of charging. In some embodiments, the method is used if there is a loss of transmission during the charging cycle.

In various other embodiments, the controller 48 can operate the array 42 without feedback from the IMD 36 to achieve the desired charging efficiency. In one embodiment, for example, the controller 48 operates the array 42 by cycling through all or some of the ultrasonic elements 44, individually or as subsets, to avoid overheating at any one location on the patient's body. In another embodiment, the controller 48 can implement known beamsteering, beamshaping, and/or beamforming techniques to adjust the acoustic energy signal from the array 42. Generally, these processes involve using the controller 48 to apply time delays on the individual elements 44 to shape and/or steer the acoustic field produced by the array 42.

In one embodiment, the beamsteering is the sweeping of the acoustic field through a series of spatial locations, thus defining the range of interrogation. In one embodiment, beamforming is the definition of the acoustic field width to match a desired region of interrogation. In one embodiment, the beam width and steering range are varied. The energy delivery device 40 can be designed with a range of beamforming and beamsteering capabilities based on its intended use. In one embodiment, variable shape ultrasonic elements 44 and/or ultrasonic elements 44 having acoustic lens/mirrors are used in conjunction with the controller 48 and methods described herein to alter the acoustic field.

Figure 5:
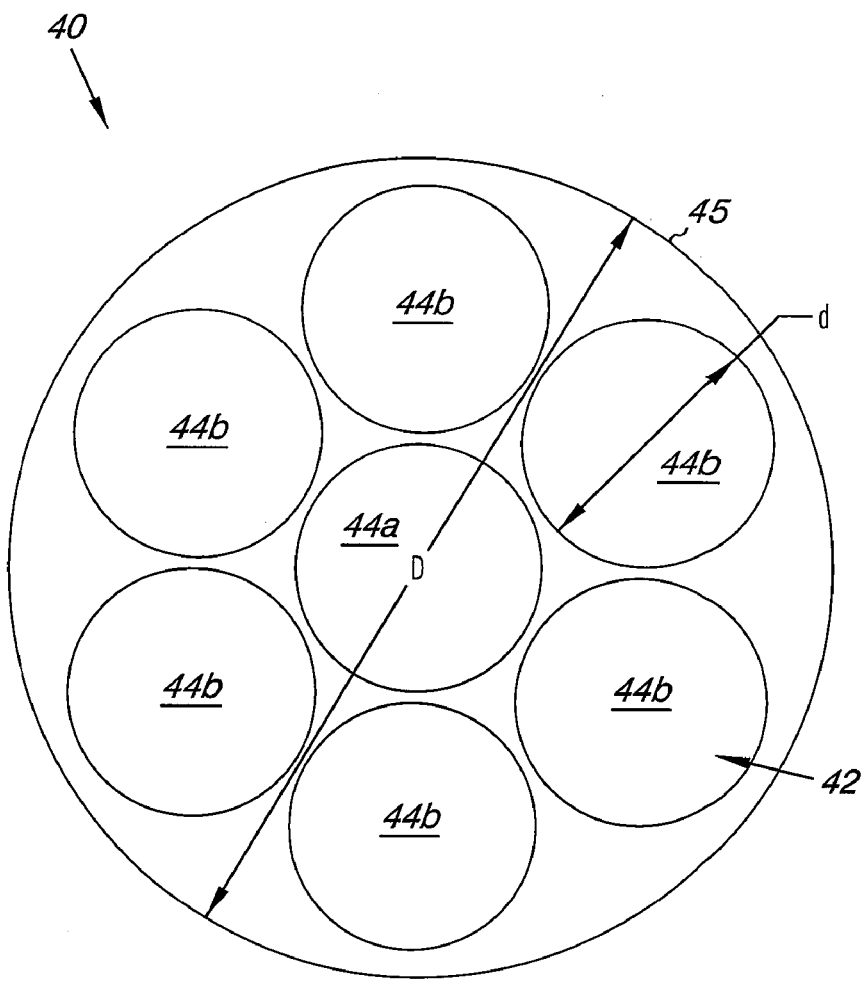
FIG. 5 is a top view of a multi-element energy delivery device according to one embodiment of the present invention.
Figure 6:
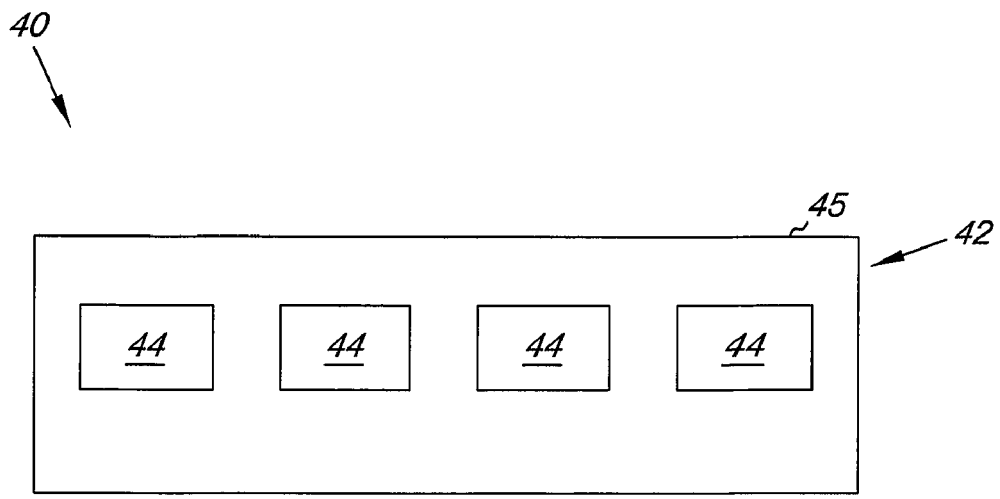
FIG. 6 is a top view of a multi-element energy delivery device according to another embodiment of the present invention.
Figure 7:
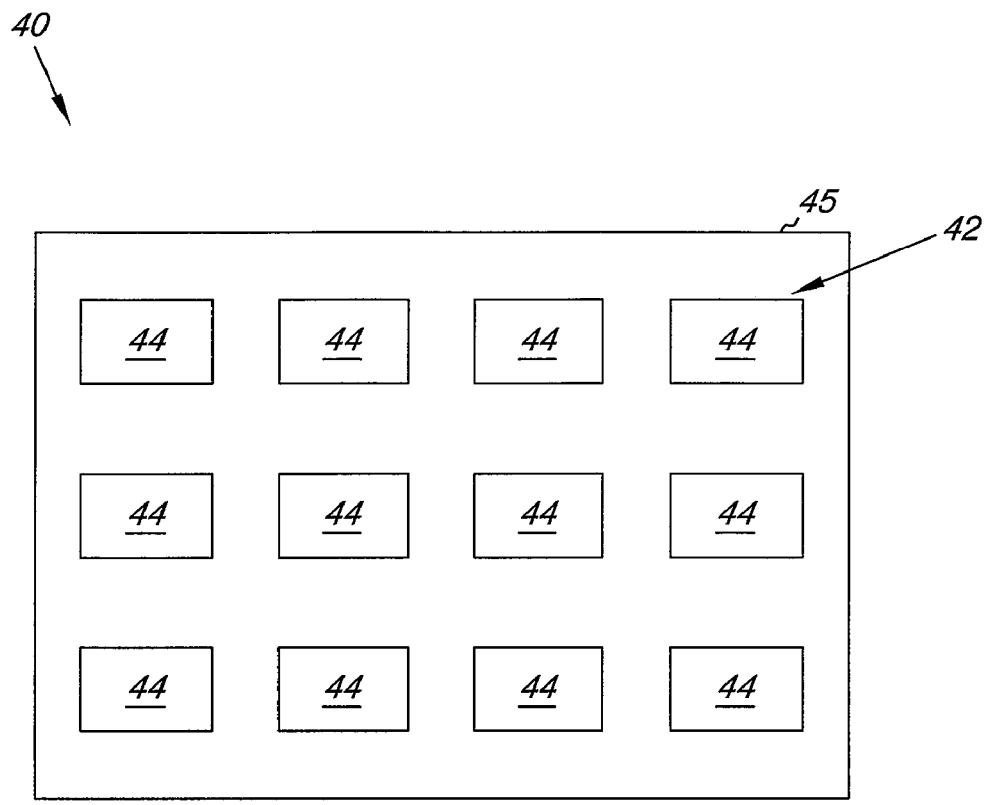
FIG. 7 is a top view of a multi-element energy delivery device according to another embodiment of the present invention.
Figure 8:
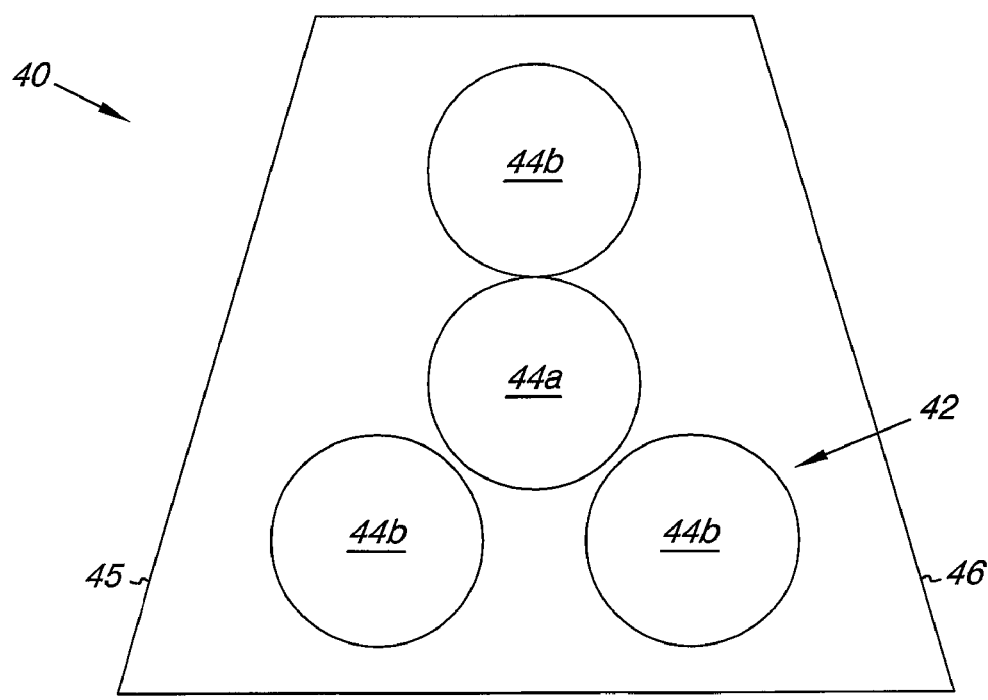
FIG. 8 is a top view of a multi-element energy delivery device according to another embodiment of the present invention.

FIG. 5 is a top view of an energy delivery device 40 according to one embodiment of the present invention. In the embodiment illustrated in FIG. 5, the energy delivery device 40 includes an array 42 of ultrasonic elements 44 located on a support structure 45. A central ultrasonic element 44a is located at the center of the support structure 45 and six additional ultrasonic elements 44b are circumferentially spaced around the central ultrasonic element 44a. In one embodiment, the energy delivery device 40 has a diameter D between about 6 and about 7.5 centimeters and a height of less than about 5 centimeters. In one embodiment, the ultrasonic elements 44 have a generally circular shape and a diameter d between about 1.8 and about 2.5 centimeters. In one embodiment, the energy delivery device 40 weighs less than about 400 grams and can be readily incorporated into a wearable garment or handheld device. In one embodiment, the energy delivery device 40 is capable of producing 40 kHz ultrasonic waves of 50 kPa at 20 centimeters of water along the maximum response axis when all of the ultrasonic elements 44 are driven in phase.

The ultrasonic elements 44 can have a variety of shapes and configurations. FIGS. 6-9 illustrate alternative embodiments of the array 42. In the embodiment shown in FIG. 6, the energy delivery device 40 has an array 42 of four rectangular ultrasonic elements 44 arranged in a linear manner. In the embodiment shown in FIG. 7, the energy delivery device 40 has an array 42 of three linearly arranged rows of rectangular ultrasonic elements 44 arranged in a three by four matrix. In the asymmetric embodiment illustrated in FIG. 8, the energy delivery device 40 has an array 42 of one central ultrasonic element 44a and a plurality of additional ultrasonic elements 44b positioned around the central ultrasonic element 44 at unequal distances from the central ultrasonic element 44a.

In the embodiments shown in FIGS. 5-8, the elements 44 are located in the same plane. In other embodiments, the acoustic beam is mechanically focused to a desired depth by configuring the ultrasonic elements 44 towards the center of an imaginary sphere such that a focus is created at the center of the sphere. For example, the ultrasonic elements 44 can be attached on a focusing structure such as a spherical shell. In another embodiment, the ultrasonic elements 44 can include an acoustic lens/mirror to mechanically focus the acoustic beam to a desired depth within the patient.

Figure 9:
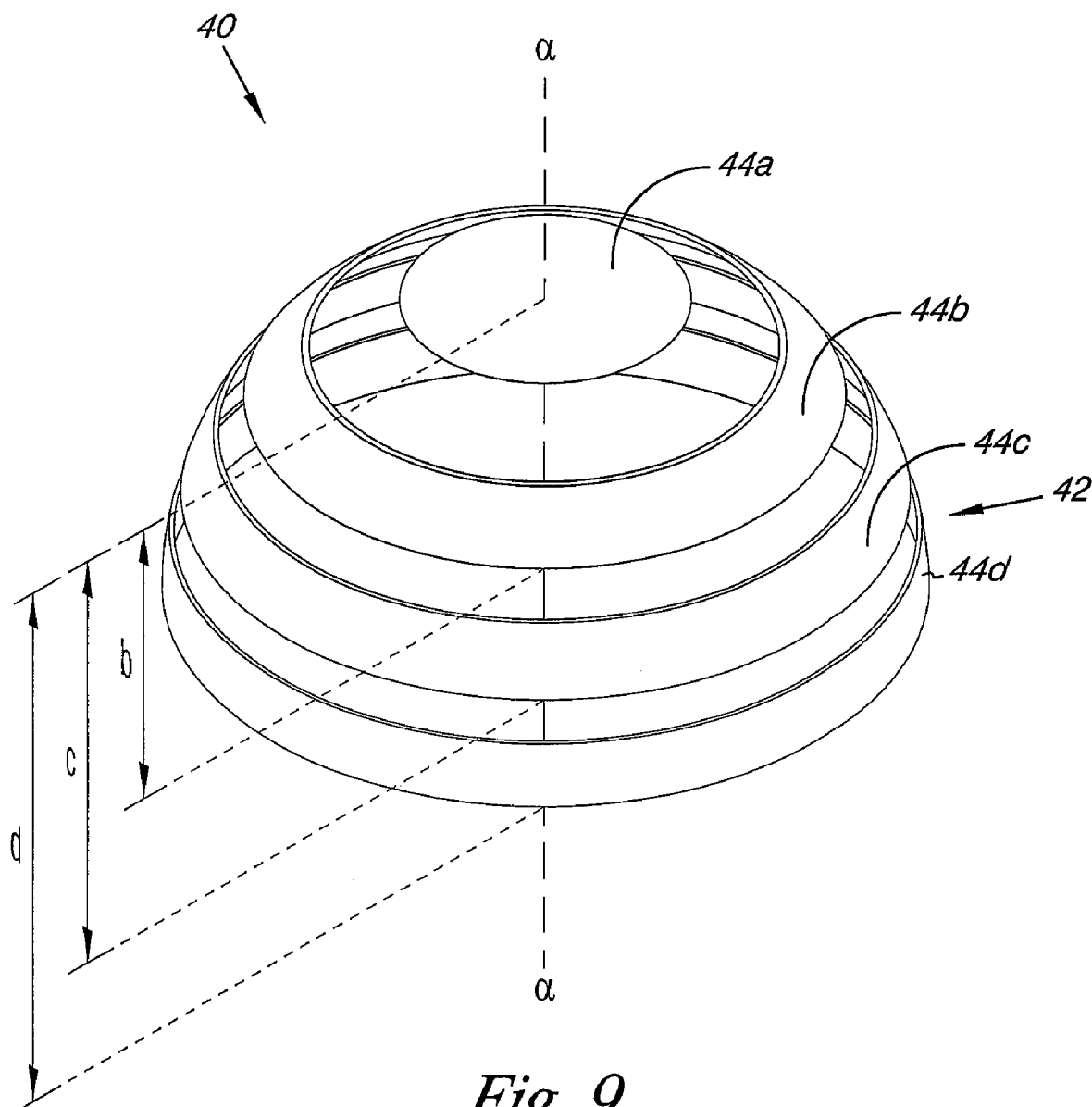
FIG. 9 is a perspective view of a multi-element energy delivery device according to another embodiment of the present invention.

FIG. 9 illustrates a dome or beehive-shaped array 42. As shown in FIG. 9, the array 42 includes a circular ultrasonic element 44a. An axis α-α that is perpendicular to the circular ultrasonic element 44a extends through the center of the circular ultrasonic element 44a. An annular ultrasonic element 44b is centered on the axis α-α and positioned along the axis α-α at a distance b from the circular ultrasonic element 44a. Similarly, an annular ultrasonic element 44c has a greater diameter than ultrasonic element 44b, is centered on the axis α-α, and is positioned along the axis α-α at a distance c from the circular ultrasonic element 44a. An annular ultrasonic element 44d has a greater diameter than ultrasonic element 44c, is centered on the axis α-α, and is positioned along the axis α-α at a distance d from the circular ultrasonic element 44a. As shown in FIG. 9, the ultrasonic elements 44b, 44c, and 44d are non-planar. In another embodiment, the ultrasonic elements 44b, 44c, 44d are planar. In yet another embodiment, the ultrasonic element 44a is non-planar.

Although FIGS. 5-9 illustrate specific numbers and configurations of ultrasonic elements 44, any number and configuration of ultrasonic elements 44 can be incorporated into the energy delivery device 40 for use in delivering acoustic energy to an implantable medical device. The array 42 can have a polygonal, a circular, or an annular configuration. The configuration can be symmetric or asymmetric about one or more axes. The ultrasonic elements 44 can have a polygonal, circular, or annular cross-sectional shape. In other embodiments, the ultrasonic elements 44 can be cylindrical, flat, or curved. In one embodiment, all of the ultrasonic elements 44 have the same shape. In other embodiments, the ultrasonic elements 44 have different shapes. For example, a central ultrasonic element 44a could have a generally circular shape and additional ultrasonic elements 44b could have a rectangular shape.

In one embodiment, the energy delivery device 40 is located on a handheld device (not shown). In another embodiment, the energy delivery device 40 is located on a wearable garment (not shown) such as a vest, shirt or belt, which can be tightly coupled to the patient's skin. The array 42 may be located directly on the handheld device or garment. Alternatively, the array 42 may be located on a support structure such as a flat plate or bed, which may or may not be coupled to a handheld device or garment.

Although the energy delivery device 40 has been described as delivering acoustic energy to a remote IMD 36, in other embodiments the energy delivery device 40 is used to deliver energy to other implantable medical devices capable of receiving acoustic energy and converting the acoustic energy to operating power. For example, the energy delivery device

40 can be used to deliver acoustic energy to a power source within a drug delivery device, a neurostimulator, a pacemaker, or a defibrillator.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. An acoustic energy delivery system for delivering acoustic energy to an implantable medical device ("IMD") located within a patient's body, the system comprising:
    an IMD including a power source and at least one ultrasonic transducer; and
    an energy delivery device configured to deliver acoustic energy for recharging the power source of the IMD, the energy delivery device including a controller and an array of ultrasonic elements electrically coupled to the controller and configured to transmit an acoustic field through the body to the IMD;
    wherein the controller is configured to selectively control one or more ultrasonic elements of the array for manipulating the acoustic field within the body based at least in part on one or more acoustic feedback signals transmitted by the at least one ultrasonic transducer of the IMD and received on the array of ultrasonic elements.

2. The system of claim 1, wherein at least one of the ultrasonic elements includes an acoustic lens or mirror.

3. The system of claim 1, wherein the array of ultrasonic elements is located on a supporting structure.

4. The system of claim 1, wherein the array of ultrasonic elements is located on a wearable garment or portable device.

5. The system of claim 1, wherein the acoustic field has a frequency of between about 20 kHz and about 200 kHz.

6. The system of claim 1, wherein the acoustic field has a frequency of about 40 kHz.

7. The system of claim 1, wherein the array has a polygonal, circular, annular, symmetric, or asymmetric configuration.

8. A method of controlling an energy delivery device for delivering acoustic energy to an implantable medical device ("IMD") located within a patient's body, the method comprising:
    sending one or more acoustic signals to the IMD, the one or more acoustic signals configured to prompt the IMD to transmit one or more responsive acoustic feedback signals to the energy delivery device;
    receiving the one or more responsive acoustic feedback signals on an array of ultrasonic elements coupled to the energy delivery device;
    processing the one or more responsive acoustic feedback signals sent by the IMD;
    operating the array of ultrasonic elements coupled to the energy delivery device based at least in part on the one or more responsive acoustic feedback signals, wherein the ultrasonic elements are electrically coupled to a controller and are configured to output an acoustic field for delivering acoustic energy to the IMD; and
    charging a rechargeable power source within the IMD using the acoustic field.

9. The method of claim 8, wherein operating the array includes operating the ultrasonic elements at a frequency of between about 20 kHz and about 200 kHz.

10. The method of claim 8, wherein operating the array includes operating the ultrasonic elements in phase.

11. The method of claim 8 wherein operating the array includes manipulating the acoustic field using any combination of adaptive beamforming, beamsteering, or beamshaping.

12. The method of claim 8, wherein operating the array includes manipulating the acoustic field using a time reversal technique.

13. The method of claim 8, wherein the method further includes detecting a change in signal amplitude or signal efficiency in the one or more responsive acoustic feedback signals, and wherein operating the array includes operating the array in response to the changed signal amplitude or signal efficiency.

14. The method of claim 8, wherein operating the array includes mechanically focusing the acoustic field to a desired depth within the patient's body.

15. The method of claim 8, wherein operating the array includes cycling one or more ultrasonic elements of the array.

16. The method of claim 8, wherein operating the array includes operating a single ultrasonic element or a subset of the ultrasonic elements.

17. A method of controlling an energy delivery device for delivering acoustic energy to an implantable medical device ("IMD") located within a patient's body, the method comprising:
    sending a number of acoustic test pulses from an IMD to an energy delivery device, the energy delivery device including an array of ultrasonic elements electrically coupled to a controller;
    entering the IMD into a charging mode of operation;
    receiving the acoustic test pulses on the ultrasonic elements of the array and computing operating parameters for use in selectively controlling one or more of the ultrasonic elements of the array based at least in part on the acoustic test pulses received on the ultrasonic elements;
    transmitting an acoustic field into the body based at least in part on the one or more operating parameters; and
    recharging a power source within the IMD.

* * * * *